United States Patent [19]

Nappholz et al.

[11] Patent Number: 5,690,690
[45] Date of Patent: Nov. 25, 1997

[54] IMPLANTABLE CARDIAC STIMULATION SYSTEM

[75] Inventors: Tibor Nappholz, Englewood; Steve Chinn, Denver, both of Colo.

[73] Assignee: Pacesetter, Inc., Sylmar, Calif.

[21] Appl. No.: 712,238

[22] Filed: Sep. 12, 1996

Related U.S. Application Data

[63] Continuation of Ser. No. 401,639, Mar. 8, 1995, abandoned.
[51] Int. Cl.⁶ .................................................. A61N 1/362
[52] U.S. Cl. .................................................. 607/30; 607/59
[58] Field of Search ................................... 607/30-32, 59, 607/60

[56] References Cited

U.S. PATENT DOCUMENTS

| | | | |
|---|---|---|---|
| 4,726,380 | 2/1988 | Vollmann et al. | 607/30 |
| 4,958,632 | 9/1990 | Duggan | 607/30 |
| 5,080,096 | 1/1992 | Hooper et al. | 607/30 |
| 5,088,491 | 2/1992 | Schaldach | 607/30 |
| 5,330,513 | 7/1994 | Nichols et al. | 607/32 |

*Primary Examiner*—William E. Kamm
*Assistant Examiner*—George R. Evanisko
*Attorney, Agent, or Firm*—Gottlieb, Rackman & Reisman

[57] ABSTRACT

A system for providing cardiac stimulation to a patient includes an implantable stimulation device with a microprocessor and a separate programmer. The stimulation device includes a memory holding substantially all the information necessary to program the device, including device specific information such as various modes of operations, the operational parameters associated with each mode, as well as patient specific information. All this information is transferred to the programmer for display and for generating a program. The program is than transferred back to the device for operating its microprocessor. In this manner, any programmer can be used to generate a program for any cardiac stimulation device without the need for providing specific programming information to the programmer for each specific device.

14 Claims, 5 Drawing Sheets

IMPLANTABLE CARDIAC STIMULATION SYSTEM

This application is a continuation of application Ser. No. 08/401,639, filed Mar. 8, 1995 now abandoned.

BACKGROUND OF THE INVENTION

A. Field of Invention

This invention pertains to a system for implantable cardiac stimulation, and more particularly to a system including an implantable cardiac stimulation device such as a pacemaker, defibrillator, cardioverter, and so on, which device includes a microprocessor for controlling the same, said system further including a universal, rather than a dedicated programmer, for programming the microprocessor. The present invention also pertains to a method of operating the improved system.

B. Description of the Prior Art

Over the last couple of decades, significant improvements have been made in the field of implantable cardiac stimulation systems including devices such as pacemakers, defibrillators, cardioverters and combinations thereof. Typically, these devices consist of a housing holding the electronic circuitry and a power supply. The electronic circuitry is connected to the heart by one or more leads terminating in electrodes. The electronic circuitry consists of an interface to the leads, and a microprocessor for analyzing the signals from the leads and for generating the signals required for stimulating the heart, depending on the function of the device. Associated with the microprocessor is a memory used for storing programmable parameters used by the microprocessor for control. The system further includes an external device to provide the programming for the microprocessor. Communication between the pacemaker and the programmer takes place over a telemetry link.

More specifically, the cardiac stimulation device includes a memory with several addresses, for holding device-specific information, such as identification and the current programming parameters. The device specific information uniquely identifies the implant by model and serial number. In order to check and modify the operation of the device, the programmer first accesses and retrieves from the device's memory its identification. The programmer than uses this information to call up from its own memory a complete set of addresses which then enable it to retrieve other specific operational characteristics of the device. This information is then displayed to the physician.

The physician is then free to review the current parameters of the device on the programmer display, and modify them, if necessary. The programmer uses the modifications to generate a new program for the device. The new program is then transmitted to the implanted device. The term "program" is used generically to describe either the actual sequence of steps required to operate the implanted device, or a set of parameters which are required by the microprocessor within the device for its operation. These parameters may include, for example, a pacing mode, upper and lower pacing limits, a rate response factor, duration of various functions such as A-V delay or PVARP, and so on.

In the existing cardiac stimulation systems, a dedicated programmer (i.e. separate software package) is provided for each type of cardiac stimulation device. Because of the lack of flexibility of the programmers, every time a device is modified, no matter how little the corresponding programmer software package has to be provided with a new set of characteristic functions associated with the modified devices.

Therefore, it can be seen that, at present, a typical cardiac stimulator system is very inflexible in that modifications of the cardiac device must be accompanied by a corresponding modification of the programmer (usually software).

Since the programmers are located either in hospitals or in the physicians' offices, upgrade of the programmers must be performed either by field personnel, who must receive special training for this task, or by a physician whose primary education is medicine, not electronics.

A further disadvantage of the existing systems is that patient specific data including historical data is stored in the programmer, and therefore this historical data is useful only if the same programmer is used every time the patient visits his doctor for a check up or other procedure.

OBJECTIVES AND SUMMARY OF THE INVENTION

In view of the above-mentioned disadvantages of the prior art, it is an objective of the present invention to provide an improved system wherein all (or part of) the information necessary for programming the implantable device, as well as the device-and patient-specific information is stored in the implantable device.

A further objective is to provide a system having a universal programmer which can be used to handle any number of different cardiac devices without the need for modifying or updating its programming.

A further objective is to provide a system wherein historic patient data may be stored on a long term basis in the implantable device.

Other objectives and advantages of the invention shall become apparent from the following description. Briefly, a system constructed in accordance with this invention includes an implantable cardiac device and a programmer. The cardiac device includes cardiac stimulation means for applying a preselected cardiac therapy. The cardiac therapy could include pacing, antiarrhythmic therapy, defibrillation, or a combination thereof. The cardiac device also includes a controller, such as a microprocessor, for controlling the cardiac stimulation means and includes memory means for storing substantially all the information required for generating the program for the microprocessor. This information may include data descriptive of the operational characteristics of the device for operating the device in one of several modes, patient specific information and so on. In order to program the device, either for setting up a new cardiac therapy, or for modifying an existing cardiac therapy, communication is first established between the device and a separate programmer. The information from the memory means is then downloaded into the programmer. The programmer may display various information related to the device and the patient to assist the physician to decide what therapy to apply. The physician then enters instructions to the programmer for defining a new or modified therapy to be used. The programmer using these instructions and the information received from the device generates a new program. This new program is uploaded to the device together with new information for defining the same. At a later time, the device can be reprogrammed using a different general purpose programmer, since all the required information is found in the implanted device.

DETAILED DESCRIPTION OF THE INVENTION

Figure 1:
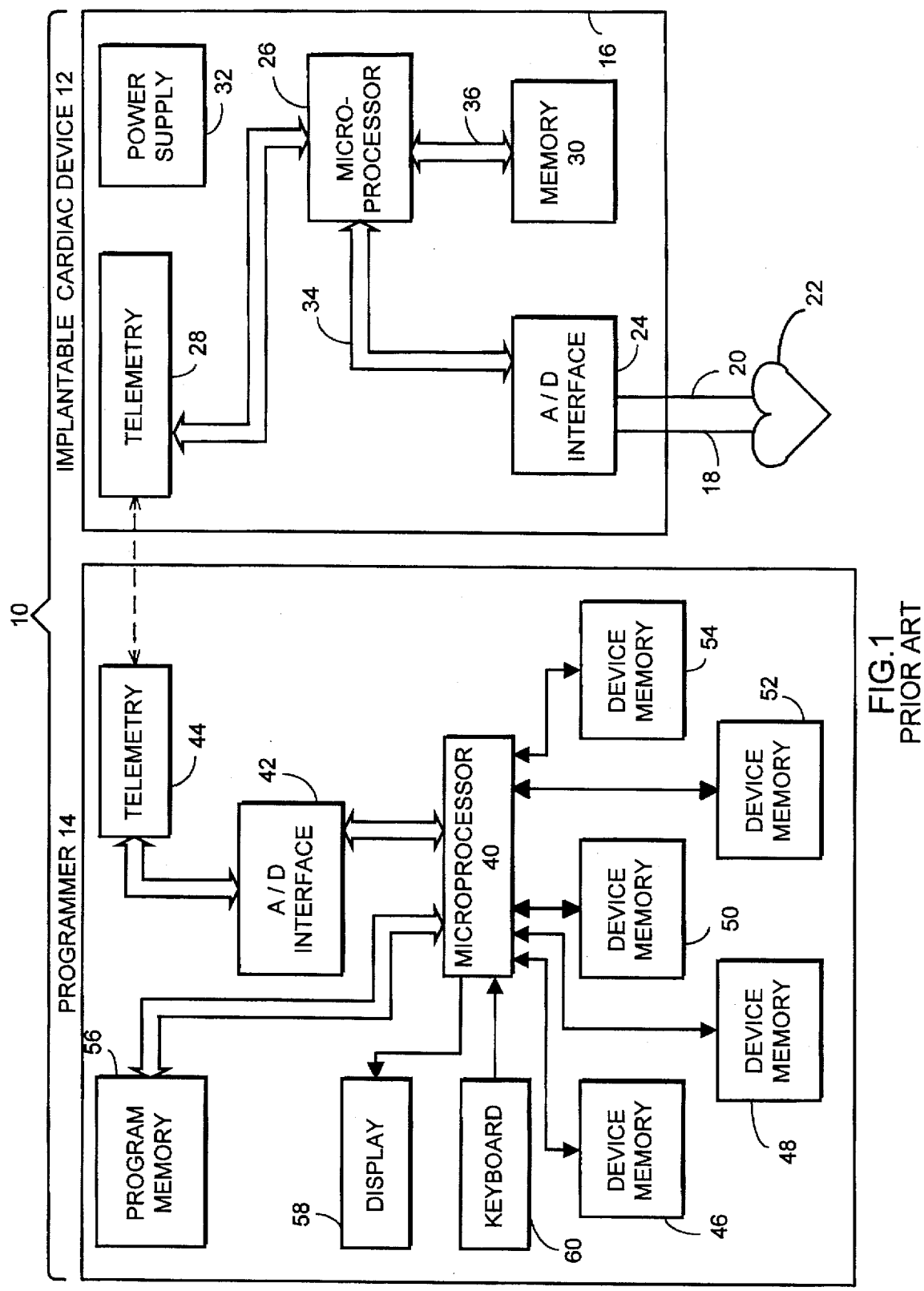
FIG. 1 shows a block diagram of a prior art cardiac stimulation system.

For a complete and accurate understanding of the present invention, it is necessary first to describe a typical prior art system. One such system is shown in FIG. 1. This prior art system 10 consists of a cardiac device 12 which may be, for example, a pacemaker, and a programmer 14. The programmer 14 may be used to program various cardiac stimulation devices, as discussed below.

Device 12 consists of a hermetically sealed implantable housing 16. Attached to the device 12 may be one or two leads 18 and 20 which extend into the chambers of a heart 22.

The device 12 includes electronic circuitry such as analog/digital interface circuit 24, a microprocessor 26, a telemetry module 28, a memory 30 and a power supply 32, all disposed in housing 16. Interface circuit 24 receives signals from leads 18, 20 which after processing go to microprocessor 26 over a bus 34 to the microprocessor 26. Information described below is exchanged between the microprocessor 26 and memory 30 over another bus 36. Power to all the circuits is provided by power supply 32.

In operation, leads 18, 20 sense electrical activity in the chambers of the heart 22. This activity is processed and, if necessary, the microprocessor 26 generates digital pulses which are converted into analog pacing signals by interface circuit 24 and applied to the heart over leads 18, 20. A detailed description of this operation can be found in co-pending U.S. application Ser. No. 226,654 filed Apr. 12, 1994, entitled FORCED ATRIOVENTRICULAR SYNCHRONY DUAL CHAMBER PACEMAKER, by T. A. Nappholz, which is incorporated herein by reference.

As mentioned above, the memory 30 is used to hold current programming parameters, as well as pacemaker specific information. Typically, the memory 30 may hold the serial number of the pacemaker, such as 0123111.

As shown in FIG. 1, the programmer 14 includes a microprocessor 40, an A/D interface 42, and a telemetry module 44. Associated with microprocessor 40 are a plurality of device memories 46, 48, 50, 52, 54 and a program memory 56. Memory 56 holds the program for the microprocessor 40. These memories are shown in separate physical blocks but can be implemented as in a large memory bank or as multiple replacement cartridges. The programmer can display instructions and various information on display 58, and commands for the microprocessor 40 can be entered on keyboard 60. Certain common subroutines are shared by the specific programming in memories 48-54 to save on memory space.

The programmer 14 can be used for any one of a plurality of cardiac devices. Each memory 46-54 is dedicated to a particular cardiac device. For example, memory bank 46 may be provided for device 12, and, accordingly, may hold the following listing. Table I contains information on specific product characteristics.

TABLE I

| DESCRIPTION | INFORMATION |
|---|---|
| SERIAL NUMBERS | 0001–10000; 20001–30,000 |
| PACER MODEL | META - DDDR 1254, 1256, 2258, 2260D ... |
| PACER STATUS | IDE, R |
| PHYSICAL INFORMATION | SIZE, WEIGHT |

The Allowed Serial Numbers in the first row refers to a list of Serial Numbers that a device is allowed to have by the manufacturer. Each specific range of serial numbers is coupled to a Model Number identified in the second row. The third row identifies the status of the device, i.e. whether it is an experimental device (identified by the FDA as an Investigative Device Exemption, IDE) or a device commercially released (R). The third row contain physical information about each device, including size, weight, etc.

In addition, memory 46 contains a second listing of other characteristics of the pacemaker 12, such as for example, various options, operational ranges and limits for various operational and programming parameters, and so on, as illustrated in Table II:

TABLE II

| CHARACTERISTIC | OPTIONS |
|---|---|
| Modes | AOO, VOO, DOO, VVIR, DDDR, DDTR |
| Minimum Rate | 50–120 in 5 ppm steps |
| Maximum Rate | 80–180 in 5 ppm steps |
| Response Rate Factor | 1–45 |
| A-V Delay | 0–200 in 20 ms steps |
| Pacing Pulse Amplitude | 2.5, 5, 7.5 V |
| Electrodes | Unipolar, Bipolar |

The first row of this table relates to the permissible modes of operation of the device 12. The second and third rows define the permissible minimum and maximum pacing rates, respectively, and also indicate the sizes of the steps for incrementing or decrementing these rates. The fourth, fifth, and sixth rows similarly pertain to permissible values for the response rate factor, A-V delay and pacing pulse amplitude, respectively. The seventh or last row indicates that the pacemaker can operate with either unipolar or bipolar leads.

Figure 2:
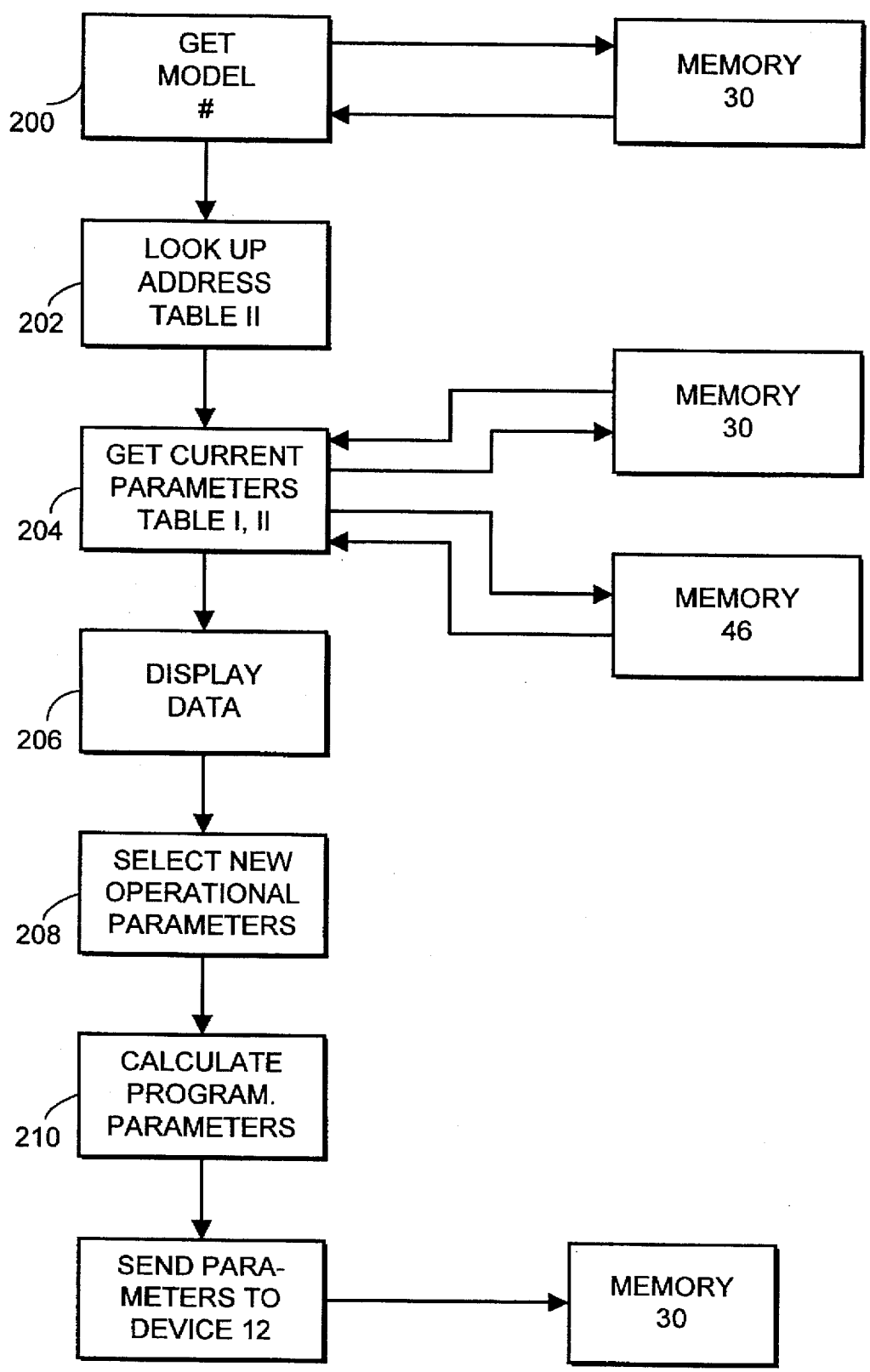
FIG. 2 shows a flow chart for the operation of the programmer of FIG. 1.

The programming of device 12 is modified as illustrated in the flow chart of FIG. 2. After communication is established between telemetry modules 28 and 44, in step 200 microprocessor 40 obtains the model number of the device 12. By convention, this information is always in a specific address of memory 30, such as 0000. Once the microprocessor 40 obtains this information, it checks to determine which of its memories 46-54 contains the information characteristic of the designated model. In the present case, the information pertaining to the model META DDDR 1254 is stored in memory 46. In step 202, the microprocessor 40 looks up the tables of device characteristics, programming parameters and options for the designated pacemaker. A partial listing of these tables are shown above as TABLE I and TABLE II.

Back to the flow chart of FIG. 2, in step 204, the various information designated by TABLE I is displayed. In step 206 the information retrieved from the memory 30, as well as the information from Table II is shown on display 58. In step 208, the physician selects the operational parameters he wants to change by entering commands on keyboard 60 for modifying the programming of device 12. As part of this step, the physician also selects different values for the parameters listed in Table I. In step 210, the microprocessor re-calculates the new programming parameters necessary to conform to the instructions received in step 208. In step 212 the new programming parameters are transmitted to the device 12 for storing in memory 30. The device 12 then can resume its operation using the new programming parameters.

As can be seen from the above description, modifying the operation of device 12 in existing systems is a time consuming operation. Moreover, if the programmer 14 is to be used for initializing or modifying the operation of various types of devices, it must contain in its memories various data specific to that device, such as the data shown in Tables I and II. If the programmer does not contain the necessary information, it must be updated.

In certain instances, it is desirable to store some patient specific historical data for long time periods for diagnostic purposes. For example it may be useful to record the patient's pacing threshold each time the patient visits his physician. At present, this type of data must be stored in the programmer, which means that the same programmer 14 must be used all the time for the same patient or access to previous programmed states in a print out. If the programmer is down during a patient visit, or the patient is at a different location, for example in an emergency, the historical data is unavailable.

Figure 3:
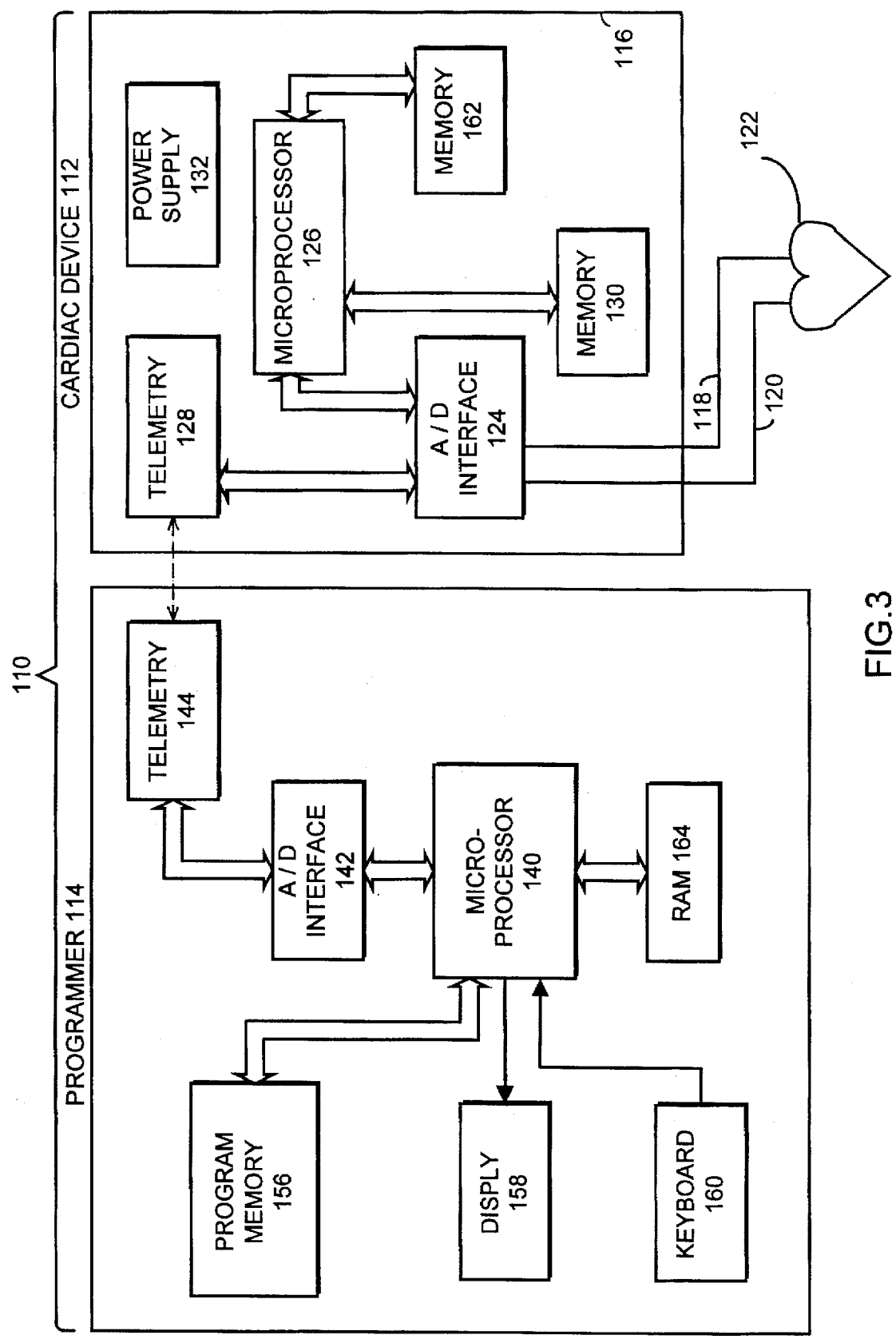
FIG. 3 shows a block diagram of a system constructed in accordance with the present invention.

A system 110 constructed in accordance with the present invention is shown in FIG. 3. For this Figure, the elements similar to the ones in FIG. 1 are identified by the same numerals preceded by a '1'. System 110 includes a device 112 enclosed in a housing 116 and having a microprocessor 126, A/D interface 124, telemetry module 128, memory 130 and power supply 132 performing the same functions as the respective counterparts of FIG. 1 except as noted below. These elements cooperate for sensing and pacing the chambers of heart 122 via leads 118 and 120.

As in FIG. 1, the system 110 includes a programmer 114 which can be used to program any one of a plurality of heart stimulating devices. The programmer 114 includes a microprocessor 140, A/D converter 142, telemetry module 144, program memory 156, display 158 and keyboard 160.

An important difference between the systems 10 and 110, is that in system 110, the device 112 also includes a second memory 162. Memory 162 is used to store substantially all the information required to program the device 112, i.e., the information originally contained in memory 46 in the device 12 of FIG. 1, and illustrated in Tables I and II. Of course, since Tables I and II are physically in the same location, i.e., within the device 112, they may be combined in a single table. In a preferred implementation memory 162 will be in ROM to ensure safety, minimum space and energy requirements. RAM is used only when absolutely unavoidable. For example, the first row may contain the identification 'Model No.' and the actual model number of the device, i.e., 'META DDDR 3000' rather than an address location in memory 130. Of course, for some parameters being used by the microprocessor 112 during its actual operation, the entry in memory 162 may still be cross-referenced to an address in memory 130. Information stored in memory 162 can be optimized by storing it in a pre-arranged framework. This is best shown below:

TABLE III

| LOCATION | I.D. | OPTIONS | START ADDRESS |
|---|---|---|---|
| 11 | MODE | 1010111 | 00000001 |
| 12 | RATE | 010111 | 00000010 |
| 13 | A_PW | 111110 | 00000011 |
| 14 | A_AMPL | 011110 | 00000100 |

| LOCATION | FORBIDDEN | STATES | |
|---|---|---|---|
| 20 | 11 | 00000010 | 010100 |
| 21 | 12 | 00010000 | 010101 |

The 'LOCATION' is the sequential location normally maintained in the ROM. The programmer then vectors to LOCATION 1 in the implant which is always in one place and is given after the opening sequence of the telemetering the subsequent locations are in sequence and correspond to standard parameters. There is normally a correspondence between 'Location" and address. Location 'O' will normally be the identification of product. Preferably all the possible options are listed, as indicated below, for modes of operation with a "1" indicating that an option is available and a "0" indicating that the option is not available, as shown below. This corresponds to the 'MODE' code in Table III. For future options not yet developed, an industry accepted conversion may be used from existing options.

TABLE IV

| AOO | 0 |
|---|---|
| AAI | 1 |
| VOO | 0 |
| VVI | 1 |
| VDI | 1 |
| DOO | 1 |
| DDI | 0 |
| DDD | 0 |

In addition, table III also contains at locations 20, 21 a listing of forbidden combinational states or operational parameters. For example, at locations 20 and 21, a listing may be stored identifying the forbidden ranges for an operational parameter, such as the rate (location 21) for a specific mode of operation, such as AAI.

This framework or data structure can be created to cover most of the options of implantable devices. Measurements and data logging can also use this approach as most of these items can be standardized. Correction factors and other pacing units can be handled in a similar manner. It is to be understood that a variety of structures are possible and the objective is to have flexibility at minimum cost of memory space.

Table V below shows a typical memory 162 with the various information required to identify a specific implant. This information is readily changed for each model without any need for changing the programmer. The use of ROM for programmer specific information is not unreasonable imposition. In the case of some data in TABLE V the full ASCII CODE may be used, such as 'MODEL NAME' to give maximum flexibility. For most other information some simple framework will allow considerable saving of space and yet provide sufficient flexibility.

TABLE V

| LOCATION | I.D. | INFO |
|---|---|---|
| 0 | MODEL | META-ATM |
| 1 | SERIAL NO. | 0123111 |
| 2 | CONFIGURATION | BIPOLAR, SSI |
| 3 | LEADS | VS 1 |
| 4 | VOLUME | 30 CC |
| 5 | DIMENSION | 6 × 45 × 51 |
| 6 | WEIGHT | 25 |

Importantly, the contents of the memory 162 may be extended to contain other information, such as a list of functions that can be monitored by the microprocessor 126. These functions then can be logged over time to generate historical data. The memory 162 may further include an indication of how much memory is available for storing the historical data.

Figure 4:
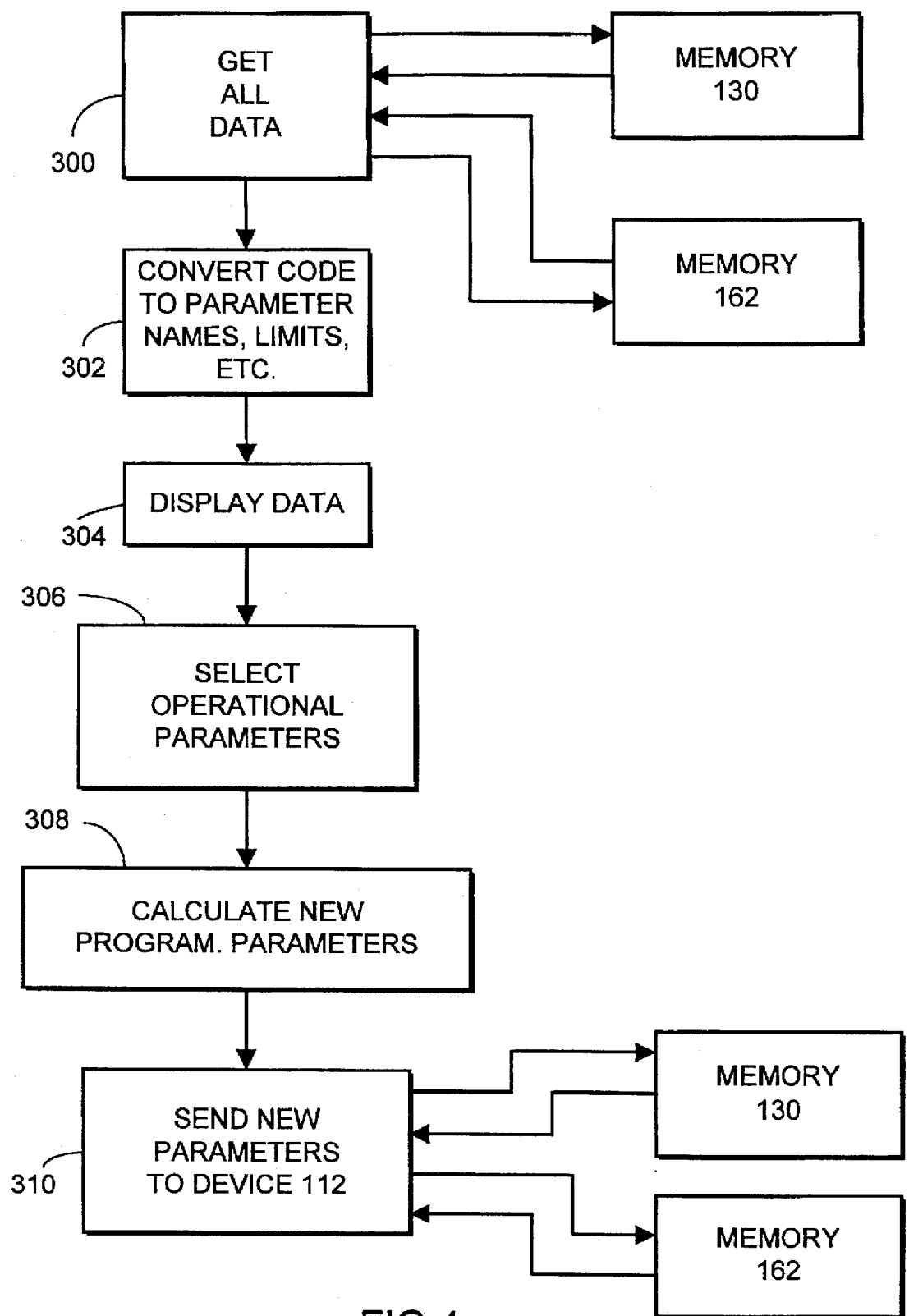
FIG. 4 shows a flow chart for the system of FIG. 3.
Figure 4A:
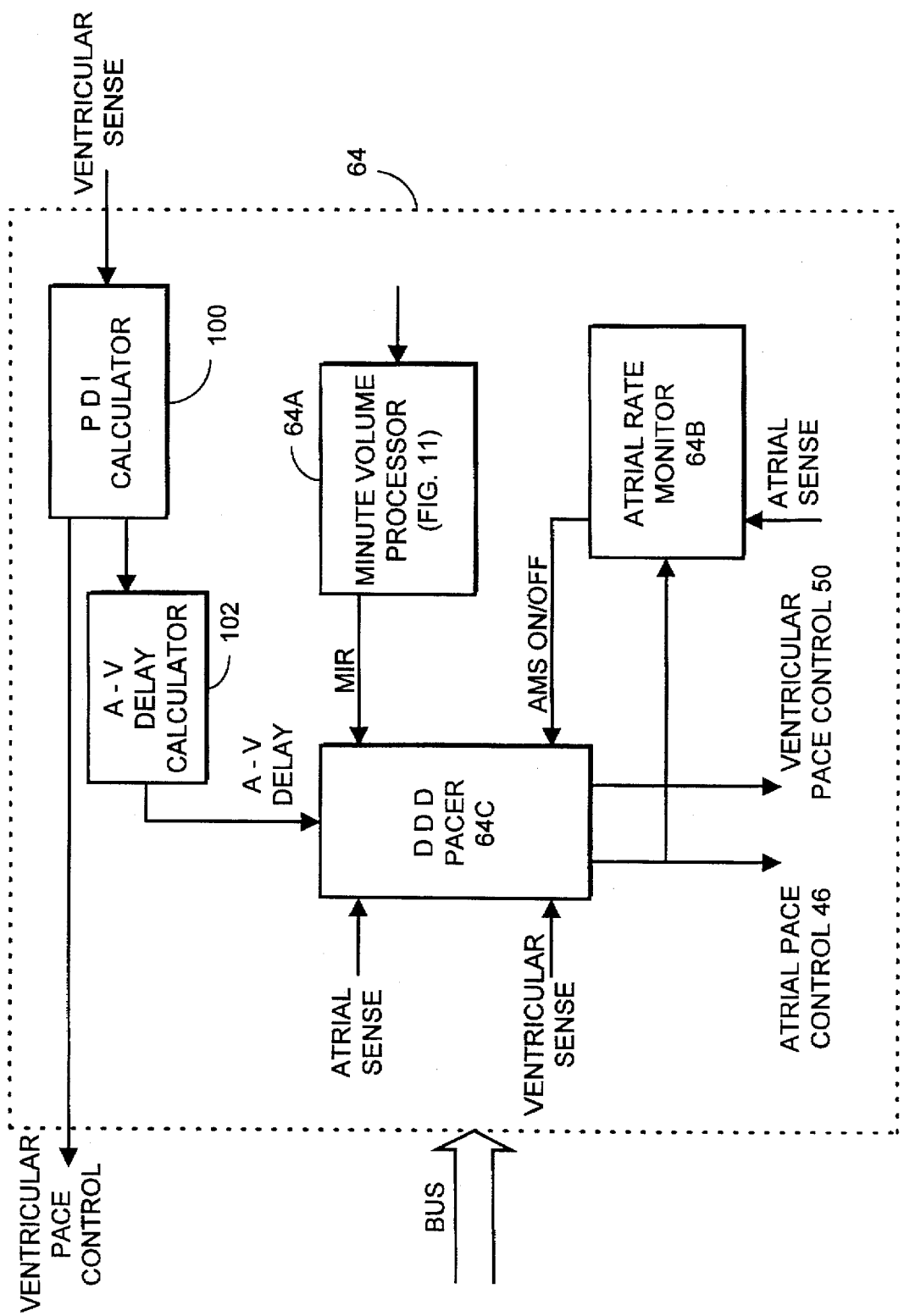

The operation of system 110 is shown in FIG. 4. Initially, programmer 114 does not contain any specific information related to the device 112. After communication is established between the programmer 114 and device 112 by telemetry modules 128, 144, in step 300 the microprocessor 140 reads all the information from memory 162 required to program device 112. Patient specific information such as the patient's name, physician and so forth, are entered into the device 112 during an initialization phase. In step 302 the received information is stored by the microprocessor 140 in a RAM (Random Access Memory) 164. In step 304 information required by the physician for initializing or modifying the device 112 is displayed on display 158. Importantly, the information can be displayed in the same format used by the present system (system 10) so that the physician need not learn any new skills for the operation of system 110. The physician selects the parameters that are to be modified in step 306, using the keyboard 160. In step 308 the microprocessor 140 calculates the new programming parameters for the device 112. In step 310 the new parameters are transmitted to the device 112. The device 112 receives the new parameters selected in step 306 or calculated in step 308. The microprocessor 126 stores the received information in memory 130 as required. The device 112 is now ready for operation.

If required, the programmer can also obtain from device 112 the information relevant for data logging. The physician may select the parameter to be logged as part of programming. These functions may include pulse threshold, ECG's, etc.

During the following visit, the historical data stored in the memory 130 is retrieved and displayed by the programmer for analysis and diagnosis.

Importantly, the programmer 114 can be used with any number of cardiac stimulation devices without the need of a priori programming or updating regarding any particular device. Similarly, the device 112 or any other heart stimulation device can be used with any other programmer without the loss of any information or flexibility of use.

Although the invention has been described with reference to a particular embodiment, it is to be understood that this embodiment is merely illustrative of the application of the principles of the invention. For example, the cardiac device has been illustrated as having two separate memories, 130, 162. However, the device may be provided with a single memory performing the same function as memories 130, 162. Accordingly, the embodiment described in particular should be considered exemplary, not limiting, with respect to the following claims.

We claim:

1. A cardiac stimulation system comprising:

a plurality of implantable cardiac devices, each device operating in accordance with a device specific program, each device including (a) a memory holding a plurality of device specific characteristics, and a list containing said characteristics, said characteristics uniquely defining cardiac devices of different types, (b) a transmitter for transmitting said list and (c) a receiver for receiving said device specific program; and a device programmer remote from said devices, said device programmer including a receiver for receiving said list, and a programming member, said programming member being provided to receive said list, and generate said device specific program in accordance with said list, said programmer including a transmitter for transmitting said device specific program to a corresponding device.

2. The system of claim 1 wherein said programmer includes display means for displaying said list.

3. The system of claim 1 wherein said memory further holds patient specific data said patient specific data being transmitted to said programmer for generating said program.

4. The system of claim 1 wherein each said device is operable in one of a plurality of modes of operation, each mode of operation being defined by a plurality of operational parameters, wherein said list of cardiac device specific characteristics include said operational parameters.

5. The system of claim 1 wherein said list of device specific characteristics includes a plurality of operational and programming parameters and ranges of values corresponding to each parameter.

6. The system of claim 1 wherein each device specific characteristic has a plurality of allowable values, and wherein said programming member generates said device specific program based on said allowable values.

7. The system of claim 6 wherein said programmer further includes data entry means for entering data, representing said values.

8. The system of claim 1 wherein each of said devices has an implantable housing, said housing including stimulation sensing means for applying cardiac stimulation and microprocessor means for controlling said stimulation sensing means in accordance with said device specific program.

9. A method of programming a plurality of cardiac stimulation devices, each device including a microprocessor for operating the device in accordance with a corresponding program and a memory holding a list of specific cardiac device parameters characteristic to said device, said parameters uniquely defining cardiac devices of different types and said program being generated by a programmer, said method comprising the steps of:

transmitting from each said device said list to said programmer;

receiving said list in said programmer and generating said corresponding program for each device in accordance with the corresponding list of parameters; and transmitting said program to the corresponding devices.

10. The method of claim 9 wherein said list includes patient specific information and wherein said step of generating said corresponding program is performed using said patient specific information.

11. The method of claim 10 further comprising displaying said patient specific information on a display during said programming step.

12. The method of claim 9 wherein said step for generating said corresponding program includes selecting a device function for monitoring over an extended time period.

13. The method of claim 12 further comprising the step of logging said function into said memory.

14. A cardiac treatment system comprising:

a plurality of implantable cardiac devices, each device including a microprocessor for operating the corresponding device in accordance with a program, a memory holding a list of specific cardiac device characteristics, said characteristics uniquely defining cardiac devices of different types, a transmitter for transmitting said list, and a receiver for receiving said program; and a generic programmer, said programmer including a receiver for receiving said lists, a program generator for generating a program for each of said devices in accordance with said lists, each program being defined by the corresponding list of cardiac device characteristics, said programmer having a transmitter for transmitting each of said programs to one of said devices.

* * * * *